(12) United States Patent
Perry et al.

(10) Patent No.: US 10,117,892 B2
(45) Date of Patent: Nov. 6, 2018

(54) DEVICES AND METHODS FOR REDUCING THE APPEARANCE OF CELLULITE

(71) Applicant: Allergan, Inc., Irvine, CA (US)

(72) Inventors: Tracy Ann Perry, Santa Barbara, CA (US); Rui Avelar, Santa Barbara, CA (US); Justin Schwab, Santa Barbara, CA (US); Zachary Dominguez, Santa Barbara, CA (US); Edwin Kayda, Santa Barbara, CA (US)

(73) Assignee: Allergan, Inc., Irvine, CA (US)

( * ) Notice: Subject to any disclaimer, the term of this patent is extended or adjusted under 35 U.S.C. 154(b) by 211 days.

(21) Appl. No.: 14/473,319

(22) Filed: Aug. 29, 2014

(65) Prior Publication Data

US 2015/0064165 A1    Mar. 5, 2015

Related U.S. Application Data

(60) Provisional application No. 61/871,600, filed on Aug. 29, 2013, provisional application No. 61/871,698, filed on Aug. 29, 2013, provisional application No. 61/874,853, filed on Sep. 6, 2013.

(51) Int. Cl.

| | |
|---|---|
| *A61K 31/728* | (2006.01) |
| *A61B 17/34* | (2006.01) |
| *A61B 17/3205* | (2006.01) |
| *A61K 38/48* | (2006.01) |
| *A61K 8/73* | (2006.01) |
| *A61Q 19/06* | (2006.01) |
| *A61B 17/32* | (2006.01) |
| *A61B 17/00* | (2006.01) |

(52) U.S. Cl.
CPC ...... *A61K 31/728* (2013.01); *A61B 17/32002* (2013.01); *A61B 17/3205* (2013.01); *A61B 17/3421* (2013.01); *A61K 8/735* (2013.01); *A61K 38/4886* (2013.01); *A61Q 19/06* (2013.01); *A61B 2017/00792* (2013.01); *A61B 2017/320028* (2013.01); *A61B 2017/3454* (2013.01); *A61K 2800/91* (2013.01); *C12Y 304/24003* (2013.01)

(58) Field of Classification Search
None
See application file for complete search history.

(56) References Cited

U.S. PATENT DOCUMENTS

| | | | |
|---|---|---|---|
| 7,588,547 B2 | 9/2009 | Deem et al. | |
| 7,601,128 B2 | 10/2009 | Deem et al. | |
| 7,811,560 B2 * | 10/2010 | Sabatino | ............ A61K 38/4886 |
| | | | 424/94.67 |
| 7,967,763 B2 | 6/2011 | Deem et al. | |
| 8,348,867 B2 | 1/2013 | Deem et al. | |
| 8,366,643 B2 | 2/2013 | Deem et al. | |
| 8,439,940 B2 | 5/2013 | Chomas et al. | |
| 8,518,069 B2 | 8/2013 | Clark, III et al. | |
| 2007/0224184 A1 | 9/2007 | Badalemente et al. | |
| 2008/0014627 A1 | 1/2008 | Merchant et al. | |
| 2008/0195036 A1 | 8/2008 | Merchant et al. | |
| 2008/0197517 A1 | 8/2008 | Merchant et al. | |
| 2008/0200863 A1 | 8/2008 | Chomas et al. | |
| 2008/0200864 A1 | 8/2008 | Holzbaur et al. | |
| 2008/0206228 A1* | 8/2008 | Vaccaro | ............... A61K 47/26 |
| | | | 424/94.67 |
| 2008/0248554 A1 | 10/2008 | Merchant et al. | |
| 2009/0275879 A1 | 11/2009 | Deem | |
| 2009/0275899 A1 | 11/2009 | Deem | |
| 2009/0326439 A1 | 12/2009 | Chomas et al. | |
| 2010/0010420 A1 | 1/2010 | Deem et al. | |
| 2010/0063006 A1 | 3/2010 | Duncan | |
| 2010/0228182 A1 | 9/2010 | Clark, III et al. | |
| 2010/0228207 A1 | 9/2010 | Ballakur et al. | |
| 2010/0256596 A1 | 10/2010 | Chomas | |
| 2011/0028898 A1 | 2/2011 | Clark, III et al. | |
| 2012/0165725 A1 | 6/2012 | Chomas et al. | |
| 2012/0277674 A1 | 11/2012 | Clark, III et al. | |
| 2013/0123767 A1 | 5/2013 | Clark, III et al. | |
| 2013/0123771 A1 | 5/2013 | Clark, III et al. | |
| 2013/0190739 A1 | 7/2013 | Clark, III et al. | |
| 2013/0190740 A1 | 7/2013 | Clark, III et al. | |
| 2013/0197427 A1 | 8/2013 | Merchant et al. | |
| 2013/0197429 A1 | 8/2013 | Clark, III et al. | |

FOREIGN PATENT DOCUMENTS

| | | | | |
|---|---|---|---|---|
| EP | 0341745 B1 * | 12/1994 | ........... | A61K 8/0208 |
| WO | 2012041512 A1 | 4/2012 | | |
| WO | WO 2012041512 A1 * | 4/2012 | ........... | A61K 9/0019 |

OTHER PUBLICATIONS

Harris Jr, Edward D., Donald R. DiBona, and Stephen M. Krane. "Collagenases in human synovial fluid." Journal of Clinical Investigation 48.11 (1969): 2104.*

Rabinowitz, Joseph L., John R. Gregg, and James E. Nixon. "Lipid Composition of the Tissues of Human Knee Joints: 11. Synovial Fluid in Trauma." Clinical orthopaedics and related research 190 (1984): 292-298.*

Engfeldt, Peter, P. Arner, and Jan Ostman. "Influence of adipocyte isolation by collagenase on phosphodiesterase activity and lipolysis in man." Journal of lipid research 21.4 (1980): 443-448.*

* cited by examiner

*Primary Examiner* — Robert J Yamasaki
(74) *Attorney, Agent, or Firm* — Nathan S. Smith; Claine Snow; McDermott Will & Emery LLP

(57) ABSTRACT

Methods and devices for use in reducing the appearance of dimpled skin or other undesirable appearance of skin in a cellulitic region of a patient are provided. The methods include the steps of disrupting fibrous septae located beneath the skin of a cellulitic region and introducing a composition beneath the skin, the composition being effective to reduce or prevent regrowth of the fibrous septae.

9 Claims, 2 Drawing Sheets

DEVICES AND METHODS FOR REDUCING THE APPEARANCE OF CELLULITE

This application claims priority to U.S. Provisional Patent Application No. 61/871,600, filed Aug. 29, 2013, and U.S. Provisional Patent Application No. 61/871,698, filed Aug. 29, 2013, and U.S. Provisional Patent Application No. 61/874,853, filed Sep. 6, 2013, the entire disclosure of each of these applications being incorporated herein by this reference.

The present invention generally relates to aesthetic surgery devices and methods and more specifically relates to devices and methods for reducing the appearance of dimpling in a cellulitic region of skin.

Gynoid lipodystrophy is a localized disorder of the subcutaneous tissue which leads to an alteration in the topography of the skin, for example, a dimpled rather than smooth appearance. This condition, commonly known as "cellulite", commonly appears on the hips, buttocks and thighs, and is not necessarily caused by being overweight, as is a common perception.

Cellulite is formed in the subcutaneous tissue, more specifically, in the subdermal fat layer below the epidermis and dermis layers. In this region, fat cells are arranged in chambers surrounded by bands of fibrous connective tissue called septae. Cellulite may be due to the generally parallel orientation of these fibrous structures, these structures being somewhat perpendicular to the skin. Fat cells held within the perimeters defined by these fibrous structures expand with weight gain and aging, for example, which stretches the septae and surrounding connective tissue. Eventually this connective tissue contracts and hardens holding the skin at a non-flexible length, while the chambers between the septae continue to expand, for example, with weight gain, or water gain. This results in areas of the skin being pulled down while adjacent sections bulge outward, resulting in the undesirable lumpy, 'orange peel' or 'cottage cheese' appearance.

In addition to application of various topical agents, a variety of other approaches for treatment of cellulite and removal of unwanted adipose tissue have been proposed. For example, mechanical massage techniques to the affected area have been tried and proposed, with the goal of breaking up lumpy tissue and/or increasing lymphatic drainage in order to smooth the appearance of skin. Methods and devices using ultrasound waves to disrupt subcutaneous tissues have also been described.

Invasive techniques, for example, liposuction, tumescent liposuction, lipolysis and the like, target adipose tissue in the subdermal and deep fat regions of the body. These techniques may include also removing the fat cells once they are disrupted, or leaving them to be resorbed by the body's immune/lymphatic system. Traditional liposuction includes the use of a surgical cannula placed at the site of the fat to be removed, and then the use of an infusion of fluids and mechanical motion of the cannula to break up the fatty tissue, and suction to "vacuum" the disrupted fatty tissue directly out of the patient. Traditional fat extraction techniques such as liposuction, target deep fat and larger regions of the anatomy and can sometimes worsen the appearance of cellulite. The subdermal fat pockets remain and are accentuated by the loss of underlying bulk (deep fat) in the region. Many times liposuction is performed and patients still seek therapy for remaining skin irregularities, such as cellulite. The tools used in these procedures often have cutting edges and are intended to dissect the subcutaneous tissue and fibrous septae. Cutting or relieving of the fibrous septae in the subdermal region by current subcision methods, is labor intensive, time consuming and techniques are highly variable. Rejoining of the severed septums, which occurs as the body naturally heals, reduces the long term effectiveness of these techniques. Techniques are still needed for more effectively reducing the appearance of cellulite.

SUMMARY

In one aspect, a method for reducing the appearance of dimpled skin or other undesirable appearance of skin in a cellulitic region of a patient is provided, the method comprising the steps of disrupting fibrous septae located beneath the skin of the cellulitic region, and introducing a composition beneath the skin of the cellulitic region, the presence of the introduced composition being effective to reduce or prevent regrowth of the disrupted fibrous septae.

The step of disrupting may comprise any suitable method or mechanism for disrupting the septae. For example, in various embodiments of the invention, this steps may comprise any one or more of severing the septae, dissolving the septae, introducing an enzyme effective to digest the septae, and/or applying laser energy to the septae.

In some embodiments, the composition to be introduced comprises a biocompatible polymer. For example, the composition may comprise a polysaccharide, for example, a hyaluronic acid, or other biocompatible polymer. The composition may further comprise an active agent, for example, an enzyme.

In another aspect, a method for reducing the appearance of cellulite in a patient is provided comprising the steps of selecting a target region of skin that has an undesirable dimpled appearance due to a cellulite condition, introducing a cannula subdermally in the patient such that a distal end of the cannula is positioned beneath the target region, moving the cannula beneath the skin to cause disruption of fibrous septae beneath the target region, introducing a composition into the target region having disrupted septae, the presence of the composition being effective to reduce or prevent regrowth of the disrupted septae.

The cannula may include a cutting or severing mechanism, for example, a blade effective to sever the septae. Alternatively or additionally, the cannula may include an energy source effective to break up the septae.

In some embodiments, the cannula includes a lumen thorough which the composition is introduced into the target region.

In yet another aspect, a device for reducing the appearance of cellulite in a patient is provided, the device comprising a tool configured to be introduced beneath skin of the patient, the tool including a distal portion effective to cause disruption of fibrous material between adipose deposits beneath the skin, and a cannula for introducing a composition beneath the skin of the patient to reduce or prevent regrowth of the fibrous material.

These and other aspects, advantages and features of the invention may be more clearly understood and appreciated with reference to the following Detailed Description and accompanying Drawings.

DETAILED DESCRIPTION

Figure 1:
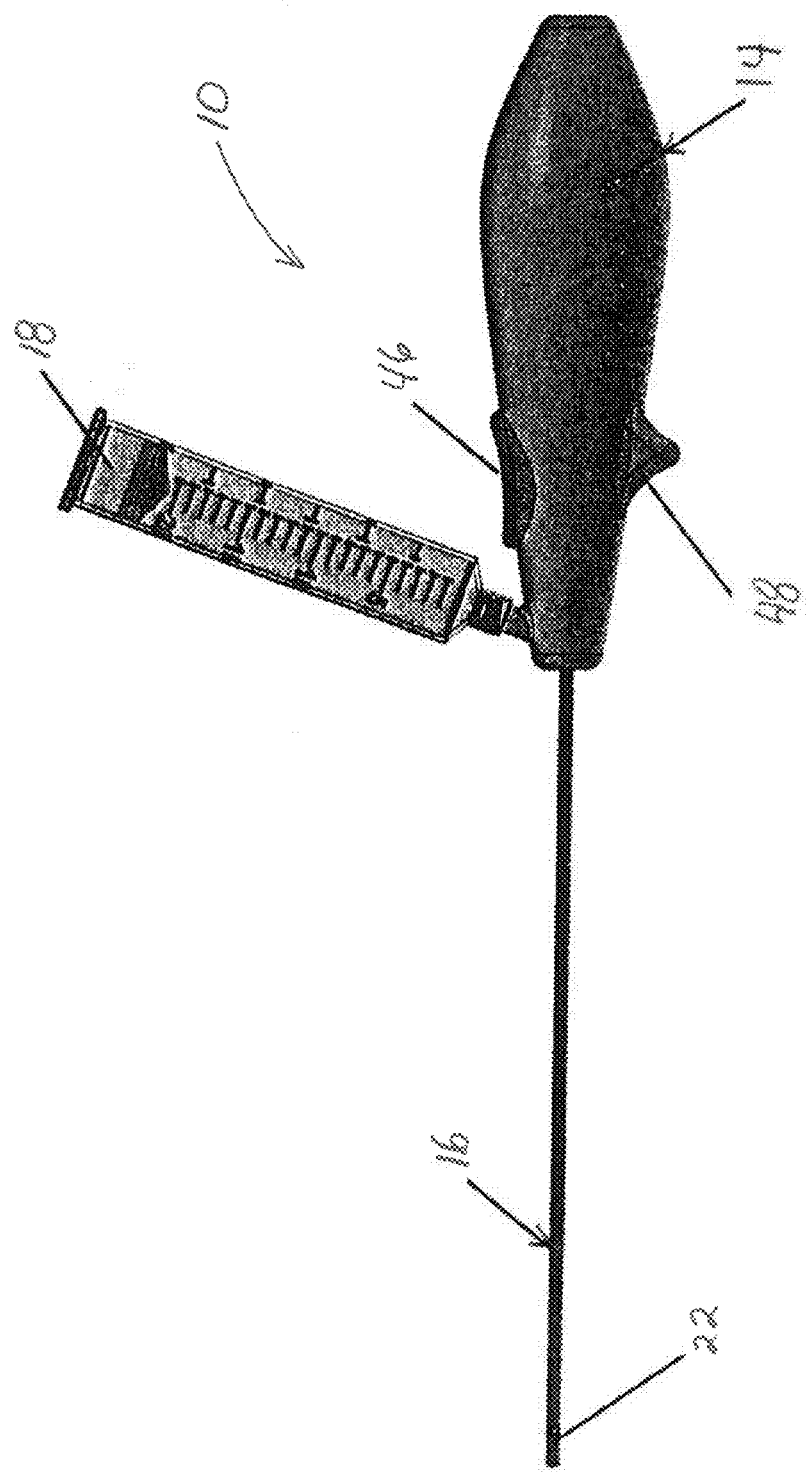
FIG. 1 is a perspective view of a device in accordance with some embodiments the invention.

The present invention provides devices and methods for treating cellulite, for example, reducing dimpling of skin commonly associated with cellulitic conditions.

In one aspect of the invention, the methods comprise the steps of disrupting fibrous septae located beneath the dimpled skin, or target region to be treated, and further, introducing a composition into the target region, wherein the presence of the composition in the target region effectively maintains the disruption of the septae, maintains separation between tissue planes after septae have been disrupted, and/or reduces or discourages regrowth or reconnection of septae.

The present cellulite treatment methods provide a longer lasting, smoother appearance to the skin than prior art methods that simply treat or attempt to sever septae without introduction of the composition. For example, the composition may be effective to cause separation of fat deposits by occupying regions previously occupied by the fibrous septae. The composition will create a separation of the fat deposits and between severed or otherwise disrupted septae, and prevent or impeded reattachment of these fibrous structures that contribute to a cellulitic appearance on the skin. With increased distance between tissue layers due to the presence of the composition, septae will further be discouraged from rejoining.

In accordance with some embodiments of the invention, disruption of the fibrous septae includes, for example, severing, diminishing, dissolving, disorganizing, extracting, destroying, weakening, or otherwise disrupting structural integrity of the septae to release the dimpling and puckering of overlying skin associated with these structures. This may be accomplished through any suitable method, for example, using minimally invasive techniques.

For example, a severing instrument may be introduced beneath the dermal layers, though a small incision or trocar, and into the fatty tissue plane. The instrument may include a sharp distal tip, or scissor-like cutting blades, which are capable of severing the fibrous septae on contact or through manipulation of levers at a handpiece. Severing of these structures releases the pull of these structures on the overlying dermal layers, which results in smoothing the appearance of the skin.

In some embodiments, a single instrument is used to perform both the steps of disrupting septae and introducing a composition. For example, a cannula may be inserted through the dermis through a single incision and into the fatty tissue plane, wherein the cannula includes both a severing element and a lumen for the introduction of the composition into the area being treated. For example, the instrument may include a cannula having a lumen terminating in an outlet for a composition to be introduced, the cannula further including a sharp distal tip, one or more blades or other mechanical cutting implement. In other embodiments, the cannula includes both a lumen and an energy source, for example, a laser source, effective to disrupt septae.

For example, in one embodiment, the present invention provides an instrument 10, such as shown in FIG. 1. The instrument 10 may include a handpiece 14, a cannula 16 and a reservoir 18 in communication with a lumen of the cannula 16, the reservoir 18 suitable for containing a quantity of the composition (not shown).

The instrument 10 includes a disrupting element 22, comprising for example, a cutting or severing mechanism 24, on a distal end of the cannula 16. The severing mechanism 24 is shown in greater detail in FIGS. 2-4. In some embodiments, severing mechanism 24 is in the form of an outer tube 32 having a hook portion 34, and a slidable, sharpened inner tube 36, with a cutting edge 38 for cutting septae hooked by the outer tube 32. In the shown embodiment, the outer tube 32 includes an side-opening, or aperture 40, having sharp edge 26, for example, a beveled edge set apart from a distal tip 44 of the cannula 16. The cannula 16 may be capped or closed at the distal tip 44.

Figure 2:
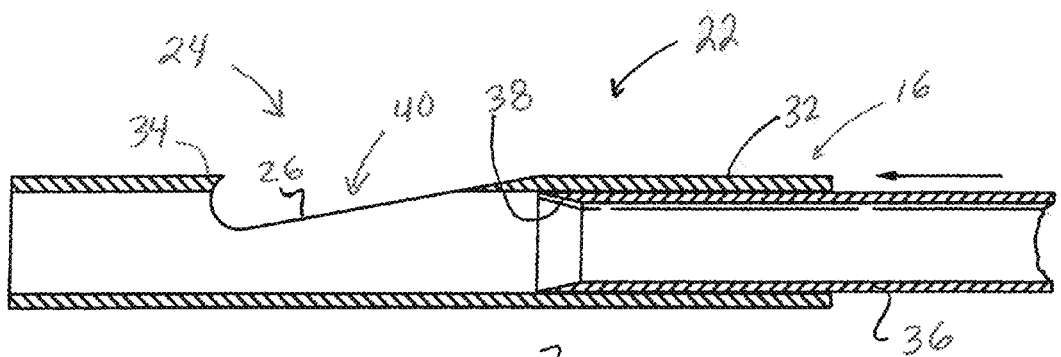
FIG. 2 is a cross sectional view of a distal end of a cannula of the device in FIG. 1, the distal end being effective to disrupt septae, the cannula being with a shown in a first position.
Figure 3:
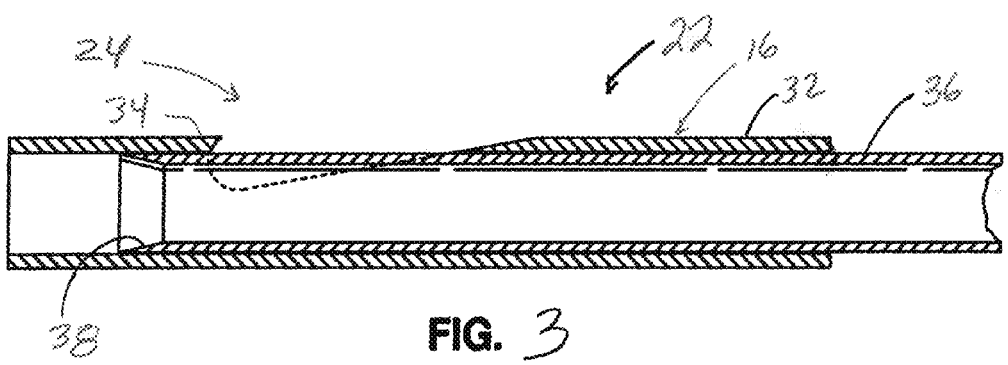
FIG. 3 is another cross sectional view of the distal end of the cannula shown in FIG. 2, the cannula being in a second position.
Figure 4:
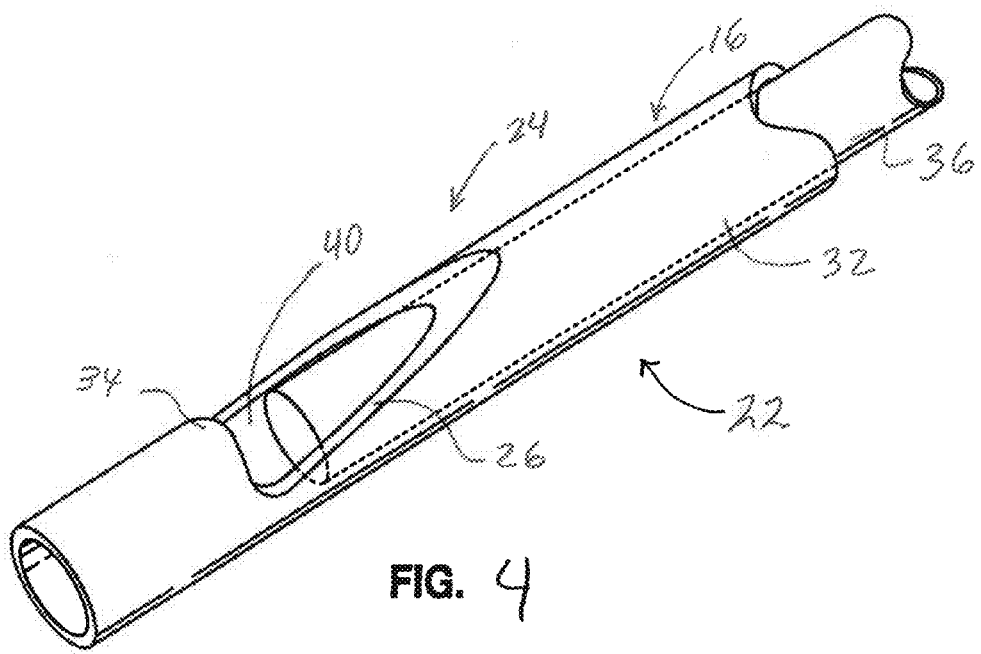
FIG. 4 is a perspective view of the cannula shown in FIGS. 2 and 3.

Once distal tip of cannula 16 is placed subdermally at a target site where septea are located, hook portion 34 is used to grasp or engage the septae. FIG. 2 illustrates the severing mechanism 24 with inner tube 36 in a first position, for example, retracted away from aperture 40, proximally with respect to outer tube 32. FIG. 3 illustrates the severing mechanism 24 in a second position, for example, with inner tube 36 in a distal or forward position relative to outer tube 32, for causing sharp edge of inner tube 36 to severe the tissue that has been drawn into or positioned in aperture 40, upon distal sliding motion of the inner tube 36 relative to outer tube 32.

Referring back to FIG. 1, while the instrument 10 is in use, the composition may flow from reservoir 18, out through the aperture 40 before, during or after the cutting process to achieve the objectives described elsewhere herein.

The handpiece 14 may comprise suitable means, for example, a trigger or switch 46 for controllably ejecting composition and/or trigger or switch 48 for operating the disrupting mechanism 22, for example, cutting action by causing back and forth sliding motion of the inner tube 36 relative to outer tube 32.

In other embodiments, the disrupting element 22 comprises a laser element (not shown) capable of providing laser energy to the septae, to cause severing or breakdown thereof.

For example, a laser instrument may be introduced into the fatty tissue plane, for example, through a trocar or small incision in skin. The laser instrument may include an element at a distal end thereof which provides focused laser energy sufficient to disrupt septae. Such an instrument can be manipulated by means of a handpiece having means for activating the laser energy in a pulsed or continuous fashion.

In another aspect of the invention, methods are provided for reducing the appearance of cellulite, the methods further comprises using visual guides or imaging techniques to assist in locating areas where significant septae may be targeted and disrupted. After disruption of the septae, the dimpled skin may rebound and smooth out rather quickly. Thus, marking the region, for example, using a medical marking pen, prior to the treatment may be of some assistance in locating areas in which placement of the composition will be most effective to maintain separation of fatty tissue planes. For example, in some embodiments, the methods comprise marking regions of the skin where specific depressions, divots or dimpling are visible. The major septae are often located directly beneath these regions, and a physician can thus target this area for breaking up the septae. In addition, by marking the skin prior to the treatment, once the septae have been severed, the marking can be used to guide the physician to the location where placement of the composition will be most effective.

The composition may then be introduced specifically into those target areas, for example, as separate deposits or boluses of material. In some embodiments, the composition is injected into the general area which has been treated in the disruption step, and if the composition has the characteristic of being sufficiently free flowing, for example, the composition will flow along the tissue planes and follow the dissection plane. Once so delivered, the composition swells, for example, by water absorption, e.g. when a hyaluronic acid based composition, and causes separation and/or spreading apart of the tissue planes.

In addition to causing spreading and/or maintaining separation of tissue planes, the amount of composition placed may be sufficient to cause a general smoothing of the overlying skin, or perhaps slightly more than that, to account for degrading or spreading of the composition after placement. Preferably, the composition should be of an amount and distribution to maintain the height of adjacent tissue planes in order to discourage septums from reattaching. This allows the two tissue planes and severed septums time to heal independently and thus discourage rejoining of septums.

In some embodiments, a more viscous composition, such as a high viscosity hyaluronic acid based composition, for example, a crosslinked hyaluronic acid gel material, is introduced between the tissue planes, while a lower viscosity, softer composition, for example, a relatively lower viscosity hyaluronic acid based composition, is deposited closer to the skin surface to provide a smooth appearance. Thus, the higher viscosity gel may provide a pillar effect to separate the tissue planes while the lower viscosity gel provides for subtle contouring.

In some embodiments, ultrasound imaging techniques may be used to assist in guiding the cannula distal tip to regions with disrupted septae for example, between tissue planes.

In embodiments of the present invention, the composition is introduced into the fatty tissue, for example, between tissue planes subsequent to, or during, disruption of the septae, to maintain separation of these planes. The composition effectively prevents, or at least impedes, regrowth of septae during the active healing phase of the tissue, for example, for at least about 2 months, for example, about 4 months, about 6 months or longer. It is contemplated that by keeping the tissue planes separated for about 6 to 8 weeks, the septae will be discouraged from reattaching. Thus, the amount and type of composition may be such that enough of the composition will remain between the tissue planes for at least about 6 to 8 weeks. Accordingly, the cellulite treatment methods of the invention maintain the smooth appearance of skin for a substantial period of time, perhaps indefinitely, when compared to many prior art treatment methods.

In some embodiments, the composition is a biodegradable, chemically or pharmacologically inert material which includes no pharmaceuticals, drugs or enzymes. In other embodiments, the composition comprises an active agent.

Preferably, the compositions are made of materials that will provide a soft, smooth, pliable consistency similar to human fatty tissue. In one aspect of the invention, the composition is a material that swells in volume upon introduction into the body. In some instances, the composition comprises a highly hydrophilic material. For example, the composition may be such that it swells about 10% or greater in volume after its introduction into the body, for example, into fatty tissue between the tissue planes.

For example, the composition may comprise a biocompatible polymer, for example, a polysaccharide, for example, a hyaluronic acid-based gel. Such hyaluronic acid gels are well known and commercial versions of such gels are commonly used as dermal fillers. Other suitable, well known, polysaccharides useful for tissue filling are also contemplated and are considered to fall within the scope of the invention. Compositions useful in accordance with the invention may include materials such as alginic acid, cellulose, collagen, elastin, gelatin and silk, and combinations thereof, and may be natural or chemically crosslinked. It is also contemplated that in some embodiments, the compositions include biocompatible materials other than polysaccharides. In some embodiments, for example, the compositions include calcium hydroxyapatite particles.

In some embodiments, the composition further comprises an active agent, for example, a pharmaceutical, drug or enzyme that will assist in preventing or impeding regrowth of septae. For example, the compositions may include collagenase, an enzyme which degrades the collagen in the fibrous connective tissue. In addition to collagenase, other enzymes may be useful in the compositions, for example, hyaluronidase, or lipolytic enzymes to encourage breaking down of adipose tissue. Other active agents useful in accordance with embodiments of the invention include anesthetics for reducing pain, such as lidocaine, vitamins and antioxidants, for encouraging healing while discouraging collagen formation, and other suitable active agents that enhance the usefulness of the invention in accordance with the objectives of reducing the appearance of cellulite and smoothing the skin.

In another aspect of the invention, methods are provided which comprise the steps of selecting a target region of skin that has an undesirable dimpled appearance due to a cellulite condition, introducing a cannula subdermally in the patient such that a distal end of the cannula is positioned beneath the target region, moving the cannula beneath the skin to cause disruption of fibrous septae beneath the target region and introducing a composition into the target region having disrupted septae, the presence of the composition being effective to reduce or prevent regrowth of the disrupted septae.

In yet another aspect of the invention, a device for reducing the appearance of cellulite in a patient is provided, the device generally comprising a tool configured to be introduced beneath skin of the patient, the tool including a distal portion effective to cause disruption of fibrous material between adipose deposits beneath the skin, and a cannula for introducing a composition beneath the skin of the patient to reduce or prevent regrowth of the fibrous material.

The present cellulite treatment compositions and methods may provide a longer lasting, smoother appearance to the skin than prior art techniques directed solely at dissolving fibrous septal structures, or physically severing these structures in fatty tissue. In contrast to such prior art, in some embodiments, the present compositions are further effective to cause physical separation of the fat deposits by occupying regions between tissue planes, for example, regions previously occupied by the dissolved septae. By maintaining this physical separation of the tissue planes 4 weeks, 6 weeks, 8 weeks or more, preferably for at least about 6 to 8 weeks, and in some embodiments, 4 months, 6 months, 8 months or longer, the fibrous bands may be discouraged from reconnecting during the healing phase, and a smooth appearance to the overlying skin will be maintained.

In accordance with some embodiments of the invention, the pharmacological agent provides chemical disruption of the fibrous septae by dissolving, weakening, diminishing, disorganizing, or otherwise disrupting structural integrity of the septae, to release the dimpling and puckering of overlying skin associated with these collagenous, fibrous structures. The pharmacological agent may be any one or more of the known agents known to chemically digest the rigid strands of connective tissue that cross the subcutaneous fatty layer and connect the dermis to the underlying fascia.

For example, the pharmacological agent may comprise any one of the agents known to enzymatically digest these septae structures. Such agents are described, for example, in Badalemente, et al., U.S. Patent Application Publication No. 2007/0224184, which is incorporated herein in its entirety by this specific reference. This document discloses that collagenase injections can be effective in lysing the collagen septae network of cellulite in humans to treat cellulite and restore a smooth skin appearance, for example, in the thigh and/or buttocks. The amount and concentration of the agent used is effective to lyse and dissolve at least a portion of the collagen septa network of the fatty tissue layers when placed in contact with these tissues.

Collagenase, such as Clostridial collagenase, is an enzyme that has specific ability to digest collagen. Collagenase suitable for use within the scope of the invention includes, for example, collagenase I and collagenase II, or any other form of collagenase useful in accordance with the objects of the invention.

Sterilized lyophilized collagenase powder is commercially available. The collagenase powder may be combined with a liquid carrier that is pharmaceutically acceptable, including inertness towards the collagenase. In one embodiment, the collagenase in the composition may be provided as a mixture of collagenase I and collagenase II in a mass ratio of about 1 to 1 and having specific activity from about 500 SRC units/mg to about 15,000 SRC units/mg, at least about 700 SRC units/mg, at least about 1000 SRC units/mg, at least about 1500 SRC units/mg. One SRC unit will solubilize rat tail collagen into ninhydrin reaction material equivalent to 1 nanomole of leucine per minute, at 25 degrees, C, pH 7.4. Collagenase has been described in ABC units as well. The potency assay of collagenase is based on the digestion of unnatured collagen (from bovine tendon) at pH 7.2 and 37 degrees C. for 20-24 hours. The number of peptide bonds cleaved are measured by reaction with ninhydrin. Amino groups released by a solubilize digestion control are subtracted. One net ABC unit of collagenase will solubilize ninhydrin reactive material equivalent to 1.09 nanomoles of leucine per minute. One SRC unit equals approximately 6.3 ABC units.

In addition, the pharmacological agent may include a lipolytic agent, for example, an adipocyte lipolytic agent known to disrupt subcutaneous fat. Such agents include phosphatidycholine, conjugated linoleic acid, forskolin nicotine, deoxycholate, theophylline, caffeine, theobromine, magnolol, isoproterenol, and other agents known to cause a reduction in the fat stores of adipocytes. The pharmacological agent may include an adipogenesis inhibitor, an ingredient capable of inhibiting the differentiation of connective tissue cells into adipocytes, or inhibiting the any one or more steps of the adipogenesis pathway. Such adipogenesis inhibitors include, for example, resveratrol, esters of resveratrol and inorganic acids such as phosphoric, sulfuric, hydrochloric acids and the like, and esters of resveratrol and carboxylic acids such as ferulic acid, hydrolyzed Myrtus Communis leaf extract, trisodium resveratrol triphosphate, resveratrol and resveratrol ferulate.

Preferably, the compositions are structured to provide a soft, smooth, pliable consistency similar to human fatty tissue. In one aspect of the invention, the polymeric component is a material that swells in volume upon introduction into the body. In some instances, the polymeric component comprises a highly hydrophilic material. For example, the composition may be such that it swells about 10% or greater in volume after its introduction into the body, for example, into fatty tissue between the tissue planes.

For example, the composition may comprise a biocompatible polymer, for example, a polysaccharide, for example, a hyaluronic acid-based gel. Such hyaluronic acid gels are well known and commercial versions of such gels are commonly used as dermal fillers. Other suitable, well known, polysaccharides useful for tissue filling are also contemplated and are considered to fall within the scope of the invention. Suitable compositions include materials such as hyaluronic acid, alginic acid, cellulose, collagen, elastin, gelatin and silk. It is also contemplated that in some embodiments, the compositions include biocompatible materials other than polysaccharides. In some embodiments, for example, the compositions include calcium hydroxyapatite particles. The polymeric component may have a viscosity that allows the spread of the relevant tissue planes when introduced inbetween these planes.

In some embodiments, the polymeric component of the composition is preferably a material which does not interact with or deactivate the active agent, for example, the collagenase. Furthermore, the polymeric component preferably is a material which can be injected into tissue, for example, using a conventional syringe or cannula, along or into the septal bands, and provide and maintain a barrier or separation between fatty tissue planes once the bands have dissolved or broken down by the agent.

In accordance with one aspect of the invention, the composition is introduced, for example, injected using a syringe, subdermally, into an area of cellulite, for example, in the thigh of a patient where the cellulite dimples are most apparent.

In some embodiments, the composition may comprise a hyaluronic acid concentration of between about 10 mg/mL and 40 mg/mL, and a collagenase in an amount to provide a potency of from between about 500 SRC units/mg to about 15,000 SRC units/mg.

To maintain stability and longevity of the composition in the tissue for a sufficient time to prevent regrowth of the septal structures, the hyaluronic acid may be chemically crosslinked, for example, with any suitable crosslinkers, for example, but not limited to, glutaraldehyde (GTA), 1-ethyl-3-(3-dimethylaminopropyl)carbodiimide (EDC), 1,4-butanediol diglycidyl ether (BDDE), (BDDE), and divinyl sulfone (DVS).

The composition effectively prevents, or at least impedes, regrowth of septae for example, for at least about 6 to 8 weeks, for example, about 2 months, for example, about 4 months, about 6 months, for example, 8 months or longer. Accordingly, the cellulite treatment methods of the invention maintain the smooth appearance of skin for a substantial period of time, perhaps indefinitely, when compared to many prior art treatment methods.

Other active agents useful in accordance with embodiments of the invention include anesthetics for reducing pain, such as lidocaine, vitamins and antioxidants, for encouraging healing while discouraging collagen formation, and other suitable active agents that enhance the usefulness of the invention in accordance with the objectives of reducing the appearance of cellulite and smoothing the skin.

In another aspect of the invention, methods are provided which comprise the steps of selecting a target region of skin that has an undesirable dimpled appearance due to a cellulite condition, introducing a cannula subdermally in the patient such that a distal end of the cannula is positioned beneath the target region, and introducing a composition of the invention into the target region, wherein the presence of the composition is effective to both dissolve, weaken or diminish the septal structures and further is effective to cause and maintain separation between the tissue planes and reduce or prevent regrowth of the septae. As tissue integration into the hyaluronic acid occurs, it is believed that this will disrupt the organized regrowth of the septae which have been weakened or dissolved by the pharmacological agent.

Visual guides or imaging techniques may be used to assist in locating areas where significant septae may be targeted. For example, marking the region, for example, using a medical marking pen, prior to the treatment may be of some assistance in locating areas in which placement of the composition will be most effective to maintain separation of fatty tissue planes. For example, in some embodiments, the methods comprise marking regions of the skin where specific, discrete depressions, divots or dimpling are visible. The compositions are then introduced into or between the fatty tissue planes or other tissues directly beneath these marked regions. For example, the compositions may be introduced generally at a suitable depth, for example, a depth of between about 0.5 cm, about 1.0 cm, to about 2 centimeters to about 6 centimeters beneath the skin surface. The compositions may be introduced as a depot generally aligning with the septal bands and between tissue planes. The amount injected may be between about 0.5 ml to about 10 ml, for example, between about 1 mL to about 6 mL, or more, or generally of an amount capable of separating the tissue planes and causing disruption of the septae. Smaller amounts may also be introduced directly beneath the dermis to smooth out contours.

EXAMPLE 1

A 32-year old healthy woman feels discouraged over the dimpled appearance of her thighs. The woman has previously lost considerable weight due to a change in diet and improvement in her exercise routine. However, her thighs, though trimmer and more toned, still maintain the undesirable dimpled appearance due to cellulite. She undergoes a procedure in accordance with the invention as follows. A skilled physician uses a marker to delineate a cellulitic target region on each of the patient's upper thighs. The physician makes specific marks on the skin at the most visible dimples. The patient is placed under general anesthesia. The physician introduces a needle or cannula, for example, through a trocar, into the fatty tissue planes beneath the marked target region. The needle or cannula includes a cutting implement at a distal tip. The physician gently but thoroughly moves the cannula or needle laterally under the skin, in a manner that causes break down and severing of the fibrous septae. The physician pays particular close attention to specific dimpled or depressed portions of the skin. Cutting of the septae directly beneath dimples or depressions in the skin causes release of tension at these areas and immediate rebounding of the skin. The physician removes the cannula or needle and introduces another cannula into the former incision or trocar. By using feel or by the markings previously made on the skin, or both, the physician uses the cannula to introduce a hyaluronic acid-based composition as a single depot that flows evenly into the dissected space where septae were severed. The patient is bandaged and allowed to go home and rest. Four months after the treatment, the patient returns to the physician and expresses satisfaction with the appearance of her thighs, which are less dimpled and substantially smoother as a result of the treatment. Two years later, her thighs still maintain their smooth appearance.

EXAMPLE 2

A 49-year old athletic, healthy woman seeks treatment for reducing the appearance of cellulite on her buttocks and thighs. She is especially discouraged over particular, discrete deep depressions and creases that seem to worsen with her age. The woman undergoes a procedure similar to the procedure described in Example 1, except that in this case, the physician uses a single instrument (such as the instrument shown in FIGS. 1-4), to perform both the cutting of the septae and the introduction of the composition (a crosslinked hyaluronic acid gel having a relatively high viscosity) between the tissue planes. (Unlike Example 1, in this Example, the physician does not need to remove the cutting instrument and then subsequently insert a separate cannula for the introduction of the composition). The treatment leaves the woman with a much smoother, younger looking appearance, with the deep depressions being much less visible. With the woman's approval, the physician further injects a small amount of a commercial dermal filler gel into the dermis where certain dimples are still somewhat apparent, using traditional dermal filling techniques. Three years later, the woman is highly satisfied with the smooth appearance of her legs and buttocks, but intermittently returns every 6 months for dermal filler injections to maintain the best results.

EXAMPLE 3

A 29-year old healthy woman feels discouraged over the dimpled appearance of her thighs. The woman has previously lost considerable weight due to a change in diet and improvement in her exercise routine. However, her thighs, though trimmer and more toned, still maintain the undesirable dimpled appearance due to cellulite. She undergoes a procedure in accordance with the invention as follows. A skilled physician uses a marker to delineate a 10 cm×10 cm cellulitic target region on each of the patient's upper thighs. The physician makes specific marks on the skin at the most visible dimples. The patient is providing with a local anesthesia in the target area. The physician introduces a needle or cannula, for example, through a trocar, into the fatty tissue planes beneath the marked target region. The physician uses the cannula to introduce a composition in accordance with the invention, as multiple depots into specific regions where septae are targeted. The patient is bandaged and allowed to go home and rest. Four months after the treatment, the patient returns to the physician and expresses satisfaction with the appearance of her thighs, which are less dimpled and substantially smoother as a result of the treatment. Two years later, her thighs still maintain their smooth appearance.

While this invention has been described with respect to various specific examples and embodiments, it is to be understood that the invention is not limited thereto and that it can be variously practiced within the scope of the invention.

What is claimed is:
1. A composition useful for reducing the appearance of dimpled skin or other undesirable appearance of skin in a cellulitic region of a patient, the composition comprising:

an injectable gel comprising:
a mixture of at least collagenase I and collagenase II in a mass ratio of 1:1, the mixture having a specific activity of at least about 500 SRC units/mg; and
at least one hyaluronic acid combined with or mixed with the collagenase I and collagenase II, the at least one hyaluronic acid present in an amount effective to provide a physical barrier between tissue planes to discourage regrowth of septal bands disrupted by the collagenase mixture: and
at least one lipolytic agent capable of causing a reduction in the fat stores of adipocytes, wherein the at least one lipolytic agent is selected from the group consisting of phosphatidylcholine, conjugated linoleic acid, deoxycholate, magnolol, and a lipolytic enzyme.

2. The composition of claim 1, the mixture having specific activity from about 500 SRC units/mg to about 15,000 SRC units/mg.

3. The composition of claim 1, the mixture having specific activity of at least about 700 SRC units/mg.

4. The composition of claim 1, the mixture having specific activity of at least about 1000 SRC units/mg.

5. The composition of claim 1, the mixture having specific activity of at least about 1500 SRC units/mg.

6. The composition of claim 1, comprising the at least one hyaluronic acid in a concentration of between about 10 mg/mL and 40 mg/mL.

7. The composition of claim 1, wherein the at least one hyaluronic acid comprises a first and a second hyaluronic acid where the first hyaluronic acid has a higher viscosity than the second hyaluronic acid.

8. The composition of claim 1, wherein the at least one hyaluronic acid is a crosslinked hyaluronic acid.

9. The composition of claim 8, wherein the at least one hyaluronic acid is crosslinked with a crosslinker selected from the group consisting of glutaraldehyde (GTA), 1-ethyl-3-(3-dimethylaminopropyl) carbodiimide (EDC), 1,4-butanediol diglycidyl ether (BDDE), and divinyl sulfone (DVS).

* * * * *